(12) United States Patent
Hamilton et al.

(10) Patent No.: US 8,445,042 B2
(45) Date of Patent: May 21, 2013

(54) XANTHAN GUM PRODUCTION FROM SUGARCANE FLUIDS

(75) Inventors: Michelle A. Hamilton Hamilton, Kingston (JM); Garth S. Dawkins, Kingston (JM); Winston A. Mellowes, St. Augustine (TT)

(73) Assignee: The University of the West Indies, Kingston (JM)

( * ) Notice: Subject to any disclaimer, the term of this patent is extended or adjusted under 35 U.S.C. 154(b) by 387 days.

(21) Appl. No.: 12/403,760

(22) Filed: Mar. 13, 2009

(65) Prior Publication Data

US 2009/0232938 A1 Sep. 17, 2009

Related U.S. Application Data

(60) Provisional application No. 61/036,205, filed on Mar. 13, 2008.

(51) Int. Cl.
*A23L 1/08* (2006.01)

(52) U.S. Cl.
USPC ........... 426/48; 426/654; 435/170; 435/253.6

(58) Field of Classification Search
None
See application file for complete search history.

(56) References Cited

U.S. PATENT DOCUMENTS 4,374,929 A * 2/1983 Weisrock et al. ............. 435/104

OTHER PUBLICATIONS

Clarke et al., In Agricultural Materials as Renewable Resources, Fuller et al., 1996, Chapter 16: Sugar Beet and Sugarcane as Renewable Resources, pp. 229-247.*
Garcia-Ochoa et al., Biotechnology Advances, 2000, vol. 18, p. 549-579.*
Yoo et al., Bioresource Technology, 1999, vol. 70, p. 105-109.*

* cited by examiner

*Primary Examiner* — Kade Ariani
(74) *Attorney, Agent, or Firm* — Wilmer Cutler Pickering Hale and Dorr LLP

(57) ABSTRACT

Disclosed herein is a method of making xanthan gum by inoculating sugarcane fluid with a bacterium that can synthesize xanthan gum, such as a bacterium of the genus *Xanthomonas*.

19 Claims, No Drawings

XANTHAN GUM PRODUCTION FROM SUGARCANE FLUIDS

CROSS-REFERENCE TO RELATED APPLICATIONS

This application claims the benefit of priority under 35 U.S.C. §119(e) to co-pending U.S. Application No. 61/036,205, filed on Mar. 13, 2008, entitled "Xanthan Gum Production from Sugarcane Fluids," which is incorporated herein by reference in its entirety.

TECHNICAL FIELD

This application relates to the field of xanthan gum production, and more particularly to a method of producing xanthan gum using sugarcane fluid.

BACKGROUND

Xanthan gum is a water soluble polysaccharide that can be used as a thickener, stabilizer, emulsifier, or suspending agent. The gum possesses a high pseudoplastic viscosity, and is resistant to wide variations in pH, temperature, and salt.

Xanthan gum is typically produced by fermenting Xanthomonas campestris in an aqueous culture medium containing at least one carbon source, a nitrogen source, a magnesium salt, phosphate ions, and other trace components. Such conventional methods can produce xanthan gum with an undesirable color, which requires bleaching or other treatments to render the xanthan gum saleable. The cost of xanthan gum manufacture depends on the raw ingredient costs and processing requirements.

It is useful to identify novel carbon sources and methods of manufacturing xanthan gum using such sources, for example, to permit manufacturing using local resources, which can result in economic benefits and greater efficiency of manufacturing.

SUMMARY

The invention relates to the finding that sugar fluid, e.g., a sugarcane fluid, is a suitable carbohydrate source for the production of xanthan gum. Accordingly, the invention includes a method for synthesizing xanthan gum. The method includes providing a production medium that includes a sugarcane fluid, and inoculating the production medium with a bacterium that can synthesize xanthan gum under conditions suitable for synthesizing xanthan gum, thereby producing conditioned production medium containing xanthan gum. In general, the bacterium is of the genus Xanthomonas, for example, Xanthomonas campestris. In some cases, the method further includes isolating xanthan gum from the conditioned production medium. The method can include a single stage fermentation, or in some cases, the method includes a multi-stage fermentation. In some embodiments, the medium is incubated in a fermentation reactor, e.g., a continuous stirred tank baffled reactor, a solids fermentation reactor, a Pumping Static-mixing loop bioreactor, a centrifugal immobilized cell bioreactor, a plunging jet reactor, a packed-bed bioreactor, a rotational fibrous-bed bioreactor, or an air bubble bioreactor.

The sugar fluid used in the method is at least one of raw sugarcane juice, heat-treated raw cane juice, limed sugarcane juice, boiled sugarcane juice, sugarcane juice treated with sulphur dioxide, sugarcane juice treated with calcium dioxide, sugarcane juice treated with polyelectrolytes, or filtered sugar cane juice. In some cases, the sugar fluid is a sugar beet fluid. In general, the sucrose concentration in the sugarcane fluid used in the method is less than or equal to 90%, for example, about 10% to about 90%, or about 10% to about 20%. In some embodiments, the concentration of glucose in the sugarcane fluid is less than or equal to 8%. In some embodiments, the concentration of fructose in the sugarcane fluid is less than or equal to 8%.

In certain embodiments of the method, the sugarcane fluid is derived from a plant of the genus Saccharum, e.g., a Saccharum officinarm L. In certain embodiments, the method further includes culturing the bacterium that can produce xanthan gum in a preculture medium comprising sugarcane fluid, thereby producing an inoculum and using the inoculum for inoculating the production medium. In some embodiments of the method, the medium includes from 0% to about 5% of one or more exogenous inorganic nutrients. In some embodiments, the exogenous inorganic nutrient is one or more of a nitrogen source, and a trace element.

In some embodiments of the method, the viscosity of the synthesized xanthan gum is about 600 cp to about 1600 cp at 20° C.

The method can also include preparing a culture of Xanthomonas campestris in a medium that includes yeast extract, malt extract, peptone, and a carbohydrate source selected from glucose, sucrose, or glucose and sucrose, thereby providing an inoculum; inoculating a medium comprising a sugarcane fluid with the inoculum, thereby producing a preculture; inoculating a medium comprising a sugarcane fluid with the preculture, thereby producing a production culture; and isolating xanthan gum from the production culture.

The invention also includes xanthan gum produced according a method described herein. The invention further includes a culture comprising a sugarcane fluid and a Xanthomonas.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Other features and advantages of the invention will be apparent from the detailed description, and from the claims.

DETAILED DESCRIPTION

Methods are described herein for a new method of producing xanthan gum by culturing a microorganism that can synthesize xanthan gum in a culture medium that contains a sugarcane fluid as its primary or sole carbohydrate source. In general, the method is carried out by preparing a preculture in a medium, e.g., a medium containing a sugarcane fluid (sugarcane preculture medium), and using the preculture to seed a sugarcane production culture medium that contains sugarcane fluid. The sugarcane production culture medium generally contains fewer additives than conventional culture media used for xanthan gum production. The production culture of the xanthan gum-producing microorganism can be carried out under conventional conditions used for producing xanthan gum. After production culture, xanthan gum is precipitated out of the medium and processed.

The new method described herein provides a method for producing xanthan gum in commercially useful quantities using a novel culture medium. The method also provides a relatively inexpensive means of producing xanthan gum, uses a medium that is simpler to prepare than conventionally used media, and permits use of locally available materials (i.e., a sugarcane fluid) for production of xanthan gum.

Preculture Medium And Production Medium

In the new method described herein, a sugar fluid is used as the basis for a culture medium suitable for production of xanthan gum. In general, the sugar fluid is derived from sugarcane and is termed herein, a "sugarcane fluid." As used herein sugarcane fluid includes raw sugarcane juice, raw sugarcane juice that has been treated for storage, heat-treated sugarcane juice, limed sugar cane juice, sugar cane juice treated with sulphur dioxide, sugar cane juice treated with calcium dioxide, sugar cane juice treated with polyelectrolytes, filtered cane juice, sugar cane juice combined with molasses. In some embodiments, the sugarcane fluid can be molasses. In some cases, a sugarcane fluid suitable for use in the method has a sucrose concentration of not more than 90% (e.g., not more than 50%, not more than 75%, or not more than 80%), a glucose concentration of not more than 8% (e.g., not more than 2%, not more than 5%), and the fructose concentration in not more than 8% (e.g., not more than 2%, not more than 5%). Both the preculture medium and production medium can use a sugarcane fluid as the carbohydrate source. In some cases, only the preculture medium or only the production medium is based on a sugarcane fluid.

Sugarcane juice is typically produced by crushing sugarcane (a *Saccharum*) with water and removing the fibrous solids (bagasse). The resulting liquid is raw sugarcane juice. The raw juice can be heated, e.g., to 70° C. to 75° C. (heat-treated sugarcane juice). Liming can be used to adjust the pH of the juice, generally to pH 7.0 (before or after heat treatment), although other methods of adjusting the pH can be used. Limed juice is clarified (for example, by settling of particulates and decanting the juice or by filtration) then concentrated (e.g., in a multi-effect evaporator), and vacuum-treated to further concentrate the juice to produce a supersaturated solution. Other treatments include boiling sugarcane juice. The juice may be treated with sulphur dioxide, calcium dioxide, or polyelectrolytes. The juice can also be filtered at any stage of production. Raw sugarcane juice can be stored using methods known in the art, for example, by adding ascorbic acid. Methods for storing sugarcane juice at other stages of treatment are also known in the art.

In some embodiments, sugar fluid includes fluid derived from sugar beet (e.g., from (*Beta vulgaris L.*) or other plant that is used for production of sugar. Suitable fluid from sugar beet includes, e.g., raw juice, juice from any stage of carbonation, thin juice, and thick juice. Methods of producing xanthan gum using non-sugarcane sugar fluid are generally the same as the methods used for sugarcane fluid.

The medium used in the new method for culturing the microorganisms to produce xanthan gum uses a sugarcane fluid as the primary carbon source, e.g., as the sole carbon source, as the source of at least 50% of the carbon in the medium, the source of at least 75% of the carbon in the medium, at least 90% of the carbon in the medium, or at least 95% of the carbon in the medium as determined by weight. In some cases, the medium is composed only of pH adjusted sugarcane fluid.

In one example, a sugarcane medium useful in the new method is composed of a sugarcane fluid, pH adjusted to 7.0 with 2N NaOH or 2N $H_3PO_4$. The medium is then autoclaved prior to use as a culture medium and then pH adjusted.

The medium can optionally include, a nitrogen source, a phosphate, a magnesium salt, and trace amounts of other components that are typically in media used for producing xanthan gum.

In some cases, an additional nitrogen source is added to a medium used in the method. Such a nitrogen source can be any nitrogen source known in the art and useful for culturing microorganisms to produce xanthan gum. Examples of such nitrogen sources include ammonium nitrate, sodium nitrate, urea, sodium glutamate, alanine, peptone, yeast extract, and malt extract. One or more such nitrogen sources can be used. Non-limiting examples of such nitrogen sources include ammonium salts and nitrate salts, (ammonium chloride, potassium nitrate, ammonium sulfate, and ammonium nitrate) arginine, casein hydrolysate, and glutamine. The nitrogen source is generally present in the culture medium in an amount of about 0.001% to about 5% by weight (e.g., 0.001% to 5% by weight), for example, in an amount of about 0.1% to about 1% by weight (e.g., 0.1% to 1% by weight) or in an amount of about 0.001% to about 0.25% by weight (e.g., 0.001% to 0.25% by weight).

Phosphate sources can optionally be added to a medium used in the new method. Such sources that can be used in a medium include, without limitation, potassium dihydrogen phosphate, dipotassium hydrogen phosphate, sodium dihydrogen phosphate, and disodium hydrogen phosphate. Phosphate is generally present in the culture medium in an amount of about 0.01% to about 5% by weight (e.g., 0.01% to 5% by weight), for example, about 0.1% to about 1% by weight (e.g., 0.1% to 1% by weight).

Optionally, magnesium salt can be included in a medium used in the new method. Examples of such magnesium salts include, without limitation, magnesium phosphate, magnesium nitrate, and magnesium sulfate. The magnesium salt is generally present in the culture medium in an amount of about 0.01 to about 1% by weight (e.g., 0.01% to 1% by weight), for example, in an amount of about 0.01% to about 0.5% by weight (e.g., 0.01% to 0.05% by weight).

In some cases, trace components are included in a sugarcane medium used in the new method. Examples of such trace components include one or more of ferrous chloride, ferric chloride, ferrous nitrate, ferric nitrate, ferrous phosphate, ferric phosphate, zinc sulfate, zinc chloride, zinc nitrate, or zinc phosphate. When a trace component is used in a sugarcane medium, the trace component is generally present in an amount of about 0.001 to about 0.01% by weight (e.g., 0.001% to 0.01% by weight), for example, about 0.001% to about 0.005% by weight (e.g., 0.001% to 0.005% by weight).

Other components can be added to a sugarcane medium so long as the sole significant carbon source is a sugarcane fluid.

The sugarcane media of the new method generally have a pH of 4.0 to 9.0, for example, a pH of about 7.0 to about 7.2 (e.g., 7.0 to 7.2).

Similar methods can be used when other sugar fluids are used, e.g., a sugar beet fluid.

Culture/Fermentation

Generally, production of xanthan gum is initiated by preparing an inoculum by culturing a microorganism that can produce xanthan gum (e.g., a *Xanthomonas*) in a small culture. The inoculum can be stored (e.g., frozen) or used soon after preparation. The inoculum is used to inoculate a sugarcane preculture medium, which is typically incubated at about 25° C. to about 30° C. In general, the culture conditions include stirring or shaking. Precultures are then used to seed a sugarcane production medium. The production medium cultures are generally incubated at 25° C. to about 30° C. for about 48 hours to about 168 hours, or until microorganism growth has reached stationary phase.

For large scale production of xanthan gum, a fermentation method is generally used such as a single stage fermentation or a multi-stage fermentation. The fermentation can be carried out using a fermentation reactor such as those that are commercially available. Examples of such reactors include a continuous stirred tank baffled reactor, a solids fermentation reactor, a Pumping Static-mixing loop bioreactor, a centrifugal immobilized cell bioreactor, a plunging jet reactor, a packed-bed bioreactor, a rotational fibrous-bed bioreactor, and an air bubble bioreactor.

Xanthan gum can be isolated from conditioned production medium using any methods known in the art. To isolate xanthan gum, the medium in which the xanthan gum-producing producing microorganism was grown (termed "conditioned medium") is clarified and sterilized, and xanthan gum is precipitated from the conditioned medium using methods known in the art, for example, by adding potassium chloride, ethanol, or isopropanol. The precipitate is recovered and subjected to further processing to produce xanthan gum powder.

Xanthan gum synthesized using a method described herein can be identified using methods known in the art, for example by the chemical composition which can be identified using, for example, analysis after acid hydrolysis, infrared spectroscopy, and physical measures. The xanthan gum produced using the new method typically has a viscosity of about 600 cP to about 1600 cP at 20° C., shear stress range 100-200 D/cm$^2$ at 20° C. (shear rate≈20 l/sec). Xanthan gum produced using sugarcane fluid is cream colored, similar to that of commercial xanthan gum. Xanthan gum produced using molasses is light brown in color.

Xanthomonas Strains

Any microorganism known to be capable of synthesizing xanthan gum can be used in the methods described herein. Examples of xanthan gum producing microorganisms of the genus Xanthomonas include X. campestris, X. carotae, X. phaseoli, X. begoniae, X. paravericola, X. translucens, X. vasculorum, X. hederae, and X. incanae. Examples of suitable X. campestris strains include, without limitation NRRL B-1459, ATCC 13951, IFO (Institute for Fermentation, Osaka) 13551, and NRRL B-1459.

EXAMPLES

The invention is further illustrated by the following examples. The examples are provided for illustrative purposes only. They are not to be construed as limiting the scope or content of the invention in any way.

Example 1

Preparation of the Primary Culture of Xanthomonas Campestris

To prepare a primary culture, a yeast malt extract broth inoculation medium was prepared. The inoculation medium contained 3 g/L yeast extract (Difco, Voigt Global Distribution Inc, Lawrence, Kans.), 3 g/L malt extract (Difco), 5 g/L peptone (Difco), and 5 g/L sucrose (Difco) adjusted to pH 7.0 with 2N $H_3PO_4$. The constituents were dissolved in 1 liter of distilled water and then 105 mL aliquots of the medium were distributed into 200 mL baffled flasks.

To initiate the primary culture, Xanthomonas campestris NRRL-B1459 (American Type Culture Collection (ATCC)) that was provided from the ATCC as freeze-dried microorganisms, was sterilely rehydrated with 0.4 mL of yeast malt extract broth. These bacteria were then transferred to a flask containing 6 mL sterile yeast malt extract broth to make a primary culture. The primary culture was incubated at 28° C. for 48 hours. The preculture for freezing was then prepared by the addition of the primary culture to a 200 mL baffled flask containing sterile medium. After incubation at 28° C. for 24 hours on a gyratory shaker at 120 rpm and amplitude 50 mm, 50% (by volume) of sterile glycerol was added to the culture. The culture was then distributed into 4 mL cryotubes in 2 mL fractions and the aliquoted primary cultures were stored at -70° C.

Example 2

Preparation of Xanthomonas Campestris Precultures

A preculture medium was prepared using sugarcane fluid that was pH adjusted to 7.0 with 2N $H_3PO_4$. One liter of the preculture medium was dispensed into a two liter baffled flask. The medium was autoclaved for 20 minutes at 121° C. then pH adjusted.

Precultures were initiated by seeding the baffled flask containing preculture medium with 100 mL of inoculation culture. The seeded culture was incubated for 24 to 48 hours at 28° C. on a gyratory shaker at 120 rpm and a ¾ inch orbital path. The culture generally reached a microorganism density of greater than $10^6$/mL.

Example 3

Production Process For Xanthan Gum

The medium used for the production process was sugarcane fluid with the pH adjusted to 7.0 with 2N NaOH and/or 2N $H_3PO_4$. Antifoam was also used during fermentation and was purchased and autoclaved before use. Antifoam was diluted and added automatically when required. The antifoam used varies with end usage. For example, for edible applications of the xanthan gum, a non-toxic antifoam is used.

To make the fermentation medium, 9 liters of pH adjusted sugarcane fluid, the sodium hydroxide solution, the phosphoric acid solution, sodium hydroxide solution, phosphoric acid solution and antifoam were added automatically during fermentation and the antifoam (together constituting the fermentation medium) were added to a fermenter. The fermentation medium was then inoculated with preculture in a ratio of 1:10.

Fermentation was carried out in a stirred tank bioreactor at 28° C. Stirring was initially 400 rpm and automatically ramped up to a maximum of 800 rpm to maintain for as long as possible a 90% dissolved oxygen concentration, and to maximize the oxygen concentration thereafter. Aeration was four liters/minute for the duration of the fermentation and the fermentation was carried out at atmospheric pressure. Additional NaOH and/or $H_3PO_4$ are added during the fermentation to maintain the pH. During fermentation, antifoam was automatically added to the fermentation culture as needed.

The fermentation time varied from about 48 to about 168 hours. The fermentation was generally terminated when there was no further significant increase in viscosity of the culture. The amount of xanthan gum recovered using ethanol varied between about 20 g/L to 36 g/L and the yield by weight with respect to the carbon source employed varies from 20% to 36%. Yield and fermentation time were at least comparable with yields using non-sugarcane fluids as a carbon source. Fermentation times were comparable to those using non-sugarcane fluid.

Other Embodiments

It is to be understood that, while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for synthesizing xanthan gum, the method comprising:
   a) culturing a bacterium that can synthesize xanthan gum in a preculture medium comprising sugarcane fluid, thereby producing an inoculum;
   b) providing a production medium comprising sugarcane fluid;
   c) inoculating the production medium with the inoculum under conditions suitable for synthesizing xanthan gum, thereby producing conditioned production medium comprising xanthan gum; and
   d) isolating the xanthan gum from the conditioned production medium, wherein the isolated xanthan gum does not require further treatment.

2. The method of claim 1, wherein the bacterium is of the genus *Xanthomonas*.

3. The method of claim 1, wherein the bacterium is *Xanthomonas campestris*.

4. The method of claim 1, wherein the method comprises a single stage fermentation.

5. The method of claim 1, wherein the method comprises a multi-stage fermentation.

6. The method of claim 1, wherein the conditioned production medium is incubated in a fermentation reactor.

7. The method of claim 6, wherein the fermentation reactor is a continuous stirred tank baffled reactor, a solids fermentation reactor, a Pumping Static-mixing loop bioreactor, a centrifugal immobilized cell bioreactor, a plunging jet reactor, a packed-bed bioreactor, a rotational fibrous-bed bioreactor, or an air bubble bioreactor.

8. The method of any one of claims 1 to 7 wherein the sugarcane fluid is at least one of raw sugarcane juice, limed sugarcane juice, boiled sugarcane juice, sugarcane juice treated with sulphur dioxide, sugarcane juice treated with calcium dioxide, sugarcane juice treated with polyelectrolytes, or filtered cane juice.

9. The method of any one of claims 1 to 6, wherein the sugarcane fluid is heat-treated raw cane juice.

10. The method of claim 1, wherein the sugarcane fluid comprises about 10% to about 60% sucrose.

11. The method of claim 1, wherein the sugarcane fluid comprises about 10% to about 20% sucrose.

12. The method of claim 1, wherein the sugarcane fluid comprises less than or equal to about 90% sucrose.

13. The method of claim 1, wherein the sugarcane fluid comprises less than or equal to about 8% glucose.

14. The method of claim 1, wherein the sugarcane fluid comprises less than or equal to about 8% fructose.

15. The method of claim 1, wherein the sugarcane fluid is derived from a plant of the genus *Saccharum*.

16. The method of claim 1, wherein the sugarcane fluid is derived from a *Saccharum officinarm* L.

17. The method of claim 1, wherein the production medium comprises 0% to about 5% of one or more exogenous inorganic nutrients.

18. The method of claim 17 wherein the exogenous inorganic nutrient is one or more of a nitrogen source, and a trace element.

19. The method of claim 1, wherein the viscosity of the synthesized xanthan gum is about 600 cp to about 1600 cp at 20° C.

* * * * *